United States Patent
Gath

(10) Patent No.: US 9,393,209 B1
(45) Date of Patent: Jul. 19, 2016

(54) PILL-ENVELOPING MATERIAL TO AID IN SWALLOWING PILLS

(71) Applicant: Shelley Corrine Gath, Arcadia, CA (US)

(72) Inventor: Shelley Corrine Gath, Arcadia, CA (US)

(*) Notice: Subject to any disclaimer, the term of this patent is extended or adjusted under 35 U.S.C. 154(b) by 107 days.

(21) Appl. No.: 14/265,190

(22) Filed: Apr. 29, 2014

Related U.S. Application Data

(60) Provisional application No. 61/886,525, filed on Oct. 3, 2013.

(51) Int. Cl.
*A61K 9/20* (2006.01)
*A61K 9/28* (2006.01)

(52) U.S. Cl.
CPC ............... *A61K 9/286* (2013.01); *A61K 9/2826* (2013.01)

(58) Field of Classification Search
None
See application file for complete search history.

(56) References Cited

FOREIGN PATENT DOCUMENTS

WO      WO 01/92400    * 12/2001

* cited by examiner

*Primary Examiner* — Tigabu Kassa
(74) *Attorney, Agent, or Firm* — Plager Schack LLP

(57) ABSTRACT

The present invention relates to a malleable, palatable pill enveloping material that becomes slippery when in contact with water or saliva making the wrapped pill easier to swallow. The enveloping material is made of a mixture of glycerin, xanthan gum, and agar which is cut into an appropriate shape for wrapping a pill.

10 Claims, 2 Drawing Sheets

PILL-ENVELOPING MATERIAL TO AID IN SWALLOWING PILLS

RELATED APPLICATION

This application claims priority to provisional patent application U.S. Ser. No. 61/886,525 filed on Sep. 30, 2013, the entire contents of which is herein incorporated by reference.

BACKGROUND

The embodiments herein relate generally to ingestible pill coatings. More specifically, embodiments of the invention are directed a malleable, digestible pill enveloping that makes ingesting the pill easier.

In today's society the generally preferred method of pharmaceutical and nutraceutical delivery is via the oral route with drugs being in pill form. However, many individuals have a difficult time swallowing the pills. This can be due to age, gag reflex, size of the pill, potential lodging of the pill in a user's throat or the general taste of the pill.

To address the difficulty that many people have in swallowing pills, efforts to develop and employ pill-enveloping materials have been undertaken. In many cases, those efforts have resulted in pills that are made in the form of capsules and gel-caps, which have a smooth and more slippery outer surface. Nonetheless, many pills are still made that do not have such an outer surface. That has resulted in after-market products that permit a user to wrap or envelop the pill in a casing that facilitates swallowing of the pill. That is a particularly useful system in the veterinarian industry, where pills are wrapped by hand before being administered. In that case, pills are often wrapped to disguise the taste and/or texture from the animal being treated.

In many cases, however, wraps used to facilitate swallowing of pills in the veterinarian context are too thick and otherwise unsuitable for human consumption. As such, there is a need for a pill wrap that provides a user the ability to encase the pill in a palatable substance to increase the ease of swallowing the pill.

SUMMARY

The present invention relates to the use of a malleable, palatable pill-enveloping material that becomes slippery when it comes in contact with water or saliva making the wrapped pill easier to swallow. The pill-enveloping material is made of a mixture of at least 50% by weight of a plastizing polyol that is soluble in water and saliva causing the pill-enveloping material to become slippery. The pill-enveloping material mixture also contains an edible polysaccharide that thickens and stabilizes the pill-enveloping material. The pill-enveloping material has a gelling agent that supports the pill-enveloping material by a support matrix.

BRIEF DESCRIPTION OF THE FIGURES

The detailed description of some embodiments of the invention will be made below with reference to the accompanying figures, wherein like numerals represent corresponding parts of the figures.

DETAILED DESCRIPTION OF CERTAIN EMBODIMENTS

Figure 1:
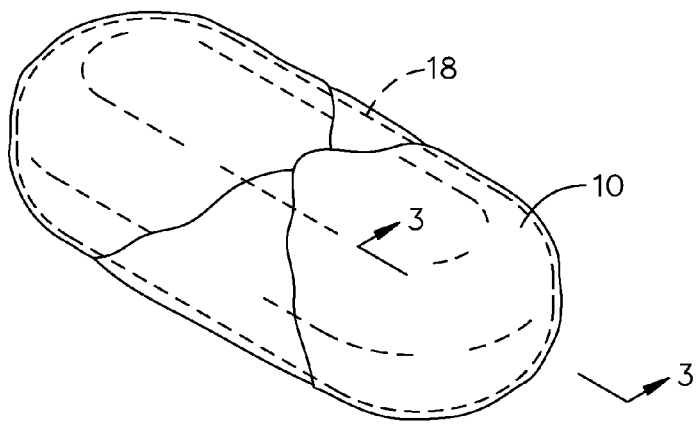
FIG. 1 shows a perspective view of one embodiment of the present invention, shown in use.

By way of example, a description of one or more embodiments of the present pill-enveloping material for encasing a pill to make it easier to swallow follows. In certain embodiments, the pill-enveloping material comprises a plastizing polyol, an edible polysaccharide and a gelling agent.

Plastizing polyols are sugar alcohols that are a colorless, odorless, viscous liquid used in many pharmaceutical and food preparations. In some embodiments, the plastizing polyol comprises glycerin. Glycerin has three hydroxyl groups that are responsible for its solubility in water and its hygroscopic nature. These properties give the pill-enveloping material the ability to become slippery when it comes in contact with water or saliva. In some embodiments, the glycerin comprises vegetable glycerin.

Edible polysaccharides are long chains of monosaccharide units bound together. The edible polysaccharides act as a food thickening agent or stabilizer to keep ingredients from separating. In some embodiments, the edible polysaccharide comprises xanthan gum. Xanthan gum acts as a thickening agent keeping the other components or the pill-enveloping material from separating Gelling agents are polysaccharides that increase the viscosity of a solution or liquid/solid mixture without substantially modifying its other properties. In some embodiments, gelling agent comprises agar. Agar is derived from the polysaccharide agarose, which forms the supporting structure in the cell walls of certain species of algae, and which is released on boiling. The agar acts as a matrix setting up a solid substrate for the pill-enveloping material. In alternative embodiments, the gelling agent comprises carrageenan. Carrageenan is a gelling agent extracted from edible red seaweed and has similar gelling properties by acting as a matrix setting up a solid substrate.

In certain embodiments, the pill-enveloping material comprises a carbohydrate. In some embodiments, the carbohydrate comprises a starch. The starch acts as a thickening and stabilizing agent for the pill-enveloping material. In some embodiments, the starch comprises corn starch. In alternative embodiments, the starch comprises non-genetically modified corn starch. In some embodiments, the starch comprises modified corn starch. In some embodiments, the starch comprises potato starch. In alternative embodiments, the starch comprises tapioca starch.

In certain embodiments, the pill-enveloping material comprises a flavoring additive. The flavoring additive increases the palatability of the pill-enveloping material making it taste appealing to the user. In some embodiments, the flavoring additive comprises sugar. In alternative embodiments, the flavoring additive comprises a sugar substitute. In some embodiments, the sugar substitute is selected from the group consisting of brazzein, curculin, erythoritol, glycyrrhizin, glycrol, hydrogenated starch hydrolysates, insulin, isomalt, lactitol, mogroside mix, mabinlin, maltitol, malto-oligosaccharide, mannitol, miraculin, monatin, monellin, osladin, pentadin, sorbitol, stevia, tagatose, thaumatin, xylitol, acesulfame potassium, aspartame, glucin, neohesperidin dihydrochalocone, saccharin, sucralose and mixtures thereof. In some embodiments the flavoring additive comprises citric acid.

In certain embodiments, the pill-enveloping material comprises a preservative. The preservative is added to prevent pill-enveloping material spoilage by inhibiting microorganism growth. In some embodiments, the preservative is selected from a group consisting of sorbic acid and its salts, benzoic acid and its salts, calcium propionate, sodium nitrite, sulfites, disodium Ethylenediaminetetraacetic acid, Butylated hydroxyanisole, Butylated hydroxytoluene, tert-Butylhydroquinone, propyl gallate, ethanol, methylchloroisothiazolinone and mixtures thereof.

In certain embodiments, the pill-enveloping material comprises a food dye. The food dye acts to provide coloration to the pill-enveloping material making it distinguishable to the user's eye. In some embodiments, the food dye comprises natural food dyes and are selected from a group consisting of Annatto, Betanin, Butterfly pea, Caramel coloring, Chlorophyllin, Elderberry juice, Lycopene, Cochineal, Pandan, Paprika, Turmeric, Saffron and mixtures thereof. In alternative embodiments, the food dye comprises artificial food dyes and are selected from a group consisting of Brilliant Blue FCF, Indigotine, Fast Green FCF, Erythrosine, Allura Red AC, Tartrazine, Sunset Yellow FCF and mixtures thereof.

Figure 2:
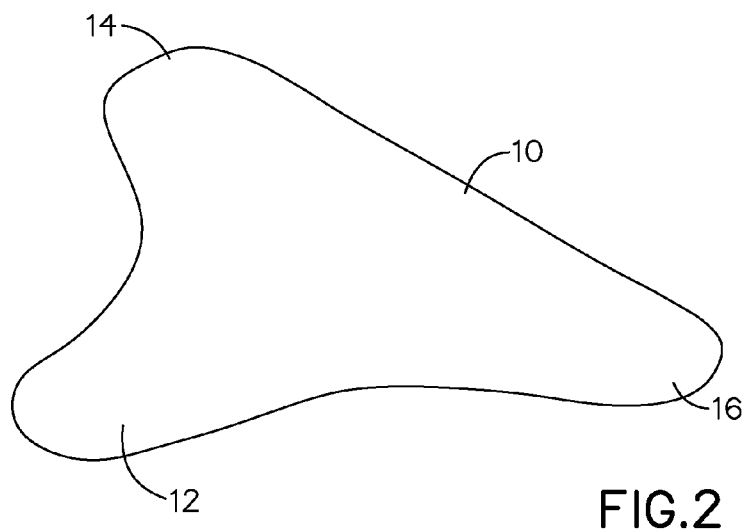
FIG. 2 shows a perspective view of the invention.
Figure 3:
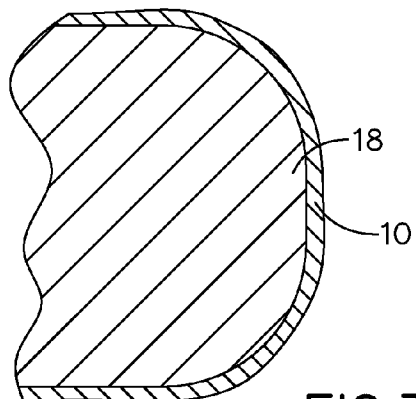
FIG. 3 shows a section view of the invention, taken along line 3-3 in FIG. 1.
Figure 4:
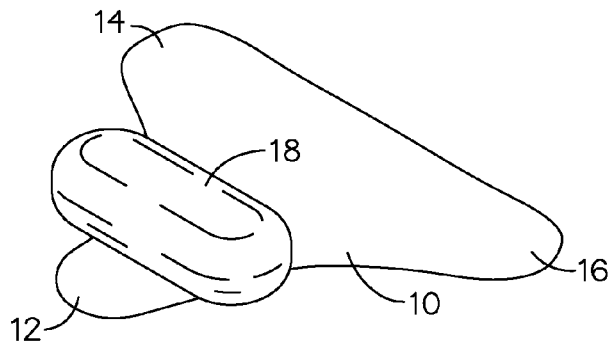
FIG. 4 shows a perspective view of the invention, illustrating the placement of 18.
Figure 5:
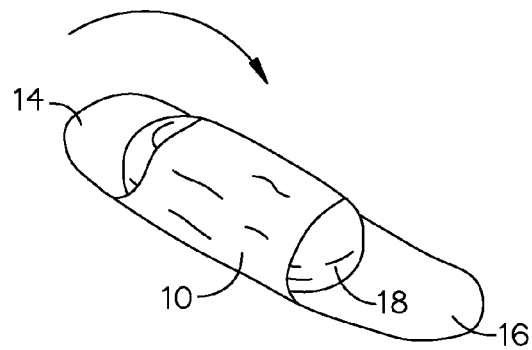
FIG. 5 shows a perspective view of the invention, illustrating the folding of 12.
Figure 6:
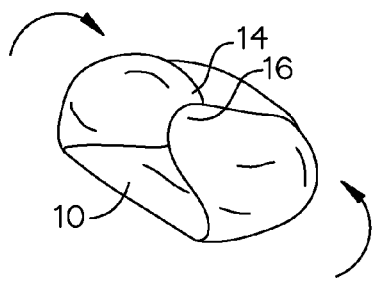
FIG. 6 shows a perspective view of the invention, illustrating the folding of 14 and 16.
Figure 7:
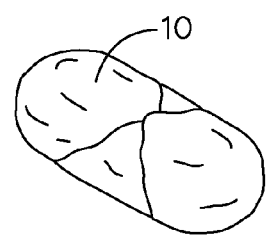
FIG. 7 shows a perspective view of the invention, illustrating 10 in its molded position.

In certain embodiments, and referring to FIG. 1, pill-enveloping material 10 is shaped and configured to envelope a pill 18. In some embodiments, the pill-enveloping material is configured to envelop any pill shape. In alternative embodiments, the pill-enveloping material is configured to wrap around any pill shape multiple times to encase the pill. In some embodiments, the pill-enveloping material is configured to double over any pill shape to account for varying pill size. In some embodiments, such as that shown in FIG. 2, the pill-enveloping material 10 is configured in a bell shape. In some cases, the bell-shaped pill-enveloping material comprises a first flap 12, a second flap 14, and a third flap 16. In alternative embodiments, the second flap and the third flap define a base of the pill-enveloping material. In some embodiments, the base of the pill-enveloping material comprises a width range of 1 centimeter to 10 centimeters. In alternative embodiments, the base of the pill-enveloping material comprises a width of 4 centimeters. In some embodiments, the first flap defines an apex of the pill-enveloping material. In alternative embodiments, the apex of the pill-enveloping material comprises a width of 0.5 centimeters to 10 centimeters. In some embodiments, the width of the apex is less than the width of the base. In alternative embodiments, the pill-enveloping material comprises a height range from base to apex of 1 centimeter to 10 centimeters. In some embodiments, the pill-enveloping material comprises a height from base to apex of 3 centimeters.

In some embodiments, such as shown in FIGS. 4-7, the pill-enveloping material 10 is configured to cover the pill 18. The first flap 12 is folded over the pill 18. The second flap 14 is folded over the pill 18 and first flap 12. The third flap 16 is folded over the pill 18, first flap 12 and second flap 14. Pressure is applied to enveloping material 10 to shape it around pill forming a continuous pill wrapped layer.

In some embodiments, the enveloping material is configured to a liquid mixture by combining the plastizing polyol, edible polysaccharide and gelling agent. In alternative embodiments, the enveloping material is configured to a liquid mixture by combining the plastizing polyol, edible polysaccharide, gelling agent, and carbohydrate. In some embodiments, the enveloping material is configured to a liquid mixture by combining the plastizing polyol, edible polysaccharide, gelling agent, carbohydrate, flavoring additive, preservative, and food dye. In alternative embodiments, the liquid mixture is configured to a strip by pouring the liquid mixture onto a sheet. In some embodiments, the sheet comprises wax paper. In alternative embodiments, the sheet comprises parchment paper. In some embodiments, the strip of liquid mixture is configured to a solid by heating the liquid mixture. In alternative embodiments, heating comprises a range of 50° F. to 200° F. In some embodiments, heating comprises 150° F. In some embodiments, the solid is configured to the bell shape of the enveloping material by cutting it from the strip after heating. In alternative embodiments, the enveloping material is configured to a thickness range of 0.1 mm to 10 mm. In alternative embodiments, the enveloping material is configured to a thickness of 1 mm.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A malleable, palatable pill-enveloping material that becomes slippery when it comes in contact with water or saliva making the wrapped pill easier to swallow, the pill-enveloping material comprising:
    a first flap configured to cover a first portion of the pill; a second flap configured to cover a second portion of the pill; a third flap configured to cover a third portion of the pill; wherein applying pressure to the first flap, the second flap, and the third flap forms a continuous pill wrapped layer around the pill; the continuous pill wrapped layer further comprising:
    at least 50% by weight of a plastizing polyol wherein the plastizing polyol is soluble in water and saliva causing the pill-enveloping material to become slippery when in contact with water and saliva;
        an edible polysaccharide wherein the edible polysaccharide thickens and stabilizes the pill-enveloping material; and
        a gelling agent wherein the gelling agent supports the pill-enveloping material by a support matrix.

2. The pill-enveloping material of claim 1, further comprising carbohydrate wherein the carbohydrate thickens and stabilizes the pill-enveloping material such that the continuous pill wrapped layer has a thickness between 0.1 mm and 10 mm.

3. The pill-enveloping material of claim 2, wherein the carbohydrate is corn starch and the thickness is 1 mm.

4. The pill-enveloping material of claim 1, wherein the plastizing polyol is vegetable glycerin and the continuous pill wrapped layer is bell shaped.

5. The pill-enveloping material of claim 1, wherein the edible polysaccharide is xanthan gum.

6. The pill-enveloping material of claim 1, wherein the gelling agent is agar.

7. The pill-enveloping material of claim 1, wherein the gelling agent is carrageenan.

8. The pill-enveloping material of claim 1, further comprising a flavoring additive wherein the flavoring additive enhances the taste of the pill-enveloping material for the user.

9. The pill-enveloping material of claim 1, further comprising a preservative wherein the preservative inhibits spoilage of the pill-enveloping material.

10. The pill-enveloping material of claim 1, further comprising a food dye wherein the food dye provides coloration to the pill-enveloping material.

\* \* \* \* \*